United States Patent [19]

Hulsmann et al.

[11] 4,188,263

[45] Feb. 12, 1980

[54] CARRIER-BOUND ACYLASES

[75] Inventors: Hans-Leo Hulsmann, Wetter, Fed. Rep. of Germany; Gustav Renckhoff, deceased, late of Witten, Fed. Rep. of Germany, by Brunhilde Renckhoff nee Grave, heir and legal representative

[73] Assignee: Dynamit Nobel Aktiengesellschaft, Troisdorf, Fed. Rep. of Germany

[21] Appl. No.: 872,277

[22] Filed: Jan. 25, 1978

[30] Foreign Application Priority Data

Jan. 29, 1977 [DE] Fed. Rep. of Germany ....... 2703703

[51] Int. Cl.$^2$ .................. C07G 7/02; C12D 13/06
[52] U.S. Cl. .................................................. 439/179
[58] Field of Search .................. 195/63, 68, DIG. 11, 195/36 P, 29; 536/32

[56] References Cited

U.S. PATENT DOCUMENTS

| | | | |
|---|---|---|---|
| 3,876,501 | 4/1975 | Hanushemsky | 195/63 X |
| 3,883,394 | 5/1975 | Savidge et al. | 195/63 |
| 3,887,432 | 6/1975 | Camthorne | 195/36 P |
| 4,119,494 | 10/1978 | Durand et al. | 195/68 |

*Primary Examiner*—David M. Naff
*Attorney, Agent, or Firm*—Sprung, Felfe, Horn, Lynch & Kramer

[57] ABSTRACT

Immobilizates of acylases (N-acyl-L-amino acid amidohydrolases) are prepared by binding the acylase to a carrier by reacting the acylase with a chemically bound reactive group of a cellulose derivative. The cellulose derivative is prepared by reaction of a hydroxyl group of cellulose with a reagent containing at least two reactive functional groups to provide the reactive group. The reaction of a hydroxyl group of cellulose and reagent is performed by contacting the reagent with cellulose dissolved in dimethyisulfoxide containing polyhydroxymethylene for reaction of the cellulose and reagent to form said derivative.

2 Claims, No Drawings

CARRIER-BOUND ACYLASES

BACKGROUND

The present invention relates to acylase immobilizates on the basis of chemically functionalized celluloses, and the preparation thereof.

The term "acylases," as used herein, refers to N-acyl-L-amino acid amidohydrolases. These are water-soluble proteins of various provenance. Preferred sources for them are either animal organs, such as pig kidneys and the pancreases of cattle, or special strains of microorganisms, such as *Aspergillus orycae*. Depending on their origin, the acylases have different substrate specificities, in that a particular species has a special facility for splitting off a particular acyl group, such as the acetyl group, for example. What is common to all acylases, however, is their ability to perform a selective deacetylation of N-acyl-L-amino acids.

The stereospecific enzymatic hydrolysis of the bond between the amino group and the acyl radical can be utilized technically for the production of L-amino acids by separating the L-amino acid liberated in the asymmetrical hydrolysis, racemizing the N-acyl-D form that has remained intact, again performing an enzymatic cleavage of the N-acyl-L part of the racemate, and pursuing the process until the N-acyl form has been used up. In this manner it is possible to transform the N-acyl racemate of the particular amino acid to the desired levorotatory form. The cleavage is accomplished under very mild conditions which cost little as regards energy input: the pH values of the substrates being cleaved are usually close to neutral, for example. The cleavage is performed as a rule at temperatures within or close to the physiological range. On account of these advantageous properties of the acylases, there is a great interest in using them to achieve an especially economical separation of the optical antipodes of amino acids on a technical scale.

The solubility of the acylases, however, is an obstacle to their technical utilization. The enzymes, which produce their action even in very low concentrations, have to be recovered to the greatest possible extent from large volumes of substrate, since they are expensive and therefore have to be reused until their enzymatic activity is exhausted.

It is necessary to remove the acylases from the cleavage solutions also in order to free them from the proteins and their soluble by-products and decomposition products. The solubility, great dilution and the chemical similarity of the acylases to their accompanying substances are obstacles, however, to an economically acceptable recovery and they considerably complicate any handling of the acylases.

Therefore, it was possible to expect insolubilized acylases to offer advantages in a biotechnology such as the enzymatic resolution of racemates: the immobilizates can be separated from the cleavage solutions by simple physical separating methods such as filtration and centrifugation, and can be recovered for reuse. They can be put into reactors, such as reactor columns for example, in the form of solid, stationary phases, which is an especially desirable arrangement for the continuous performance of the optical cleavage. Furthermore, enzymes fixed on carriers are often more stable thermally than the soluble forms, they permit in some cases operation at higher temperatures to increase the volume-time yield of the process, and they are often less sensitive to denaturing influences.

Consequently, enzymes made insoluble by applying them to carrier materials have already been proposed.

The carriers which have hitherto been proposed for the insolubilization of cleavage-active biogenic proteins, however, do not satisfy to the desired degree the requirements which must be met by the immobilizates used in an industrial process. The reasons for this are as follows:

Inorganic carriers of a mainly hydrophobic character, such as porous glasses for example, do have better mechanical properties than many hydrophilic organic carriers. The binding capacity of inorganic carriers for the bioactive proteins, however, is very limited. In contact with the neutral to weakly alkaline substrate solutions, the enzyme activity diminishes so greatly that these immobilizates are unsuitable for technical application. Also, such carrier materials often have excessively high solubilities in the substrate solutions; the result is poor stability of the fixed enzyme and contamination of the cleavage solutions. Hydrophilic carriers, such as modified polysaccharides or polyacrylamide gels, prove to have very undesirable, sometimes irreversible swelling phenomena, and often they have porosity caused by swelling, so that a rapid transformation of the substrates is impossible due to interference with the diffusion. The swelling phenomena are especially disadvantageous when the gel-like immobilizates are used in solid-bed reactors. Acylase adsorptively fixed to DEAE Sephadex, a dextran provided with diethylaminoethyl groups, or to DEAE cellulose, does not adhere strongly enough to achieve sufficient half-value times for their hydrolytic activity. The polar bond content developed in the formation of such immobilizates does not attain the strength and insensitivity to milieu factors, such as internal concentration and internal charge, of covalently bound enzymes.

The use of cellulose or cellulose derivatives as carriers has been impeded generally by the fact that cellulose is insoluble without chemical alteration, and the reactions performed in suspended phase require drastic conditions, and lead to no more than partial reactions on account of the tangling of the cellulose chains.

Chemically modified cellulose, such as alkali celluloses, can be functionalized with only a few reagents and are hard to free from the harmful alkalies. Immobilizates on the basis of the known modified celluloses are also easily oxidizable and have to be handled with the exclusion of air.

THE INVENTION

The problem accordingly existed of producing acylase immobilizates in which the enzyme is largely covalently bound. The fixed acylases are to have sufficient activity and sufficient stability of their activity, they must have improved mechanical and hydrodynamic properties, and they are to require an easily available starting material as the carrier.

This problem is solved by the invention in that acylases are reacted by reactions known in themselves with chemically bound reactive groups of cellulose derivatives which have been prepared by reaction of cellulose in solutions in dimethylsulfoxide containing polyhydroxymethylene, with an at least bifunctional reagent in accordance with application Ser. No. 838,432, filed Sept. 30, 1977 (lodged in Group 141), now U.S. Pat. No.

4,137,399, which application is incorporated herein by reference.

In contradistinction to the known chemical modification of cellulose by reactions in the heterogeneous phase, e.g., in the manner of a boundary surface reaction, the functionalization of the cellulose homogeneously dissolved in an inert solvent in accordance with Ser. No. 838,432, under anhydrous conditions, permits the introduction of numerous and varied reactive groups which by conventional methods are difficult or impossible to introduce, and makes it possible to select the degree of substitution of the cellulose hydroxyl groups.

These are two important requirements for the preparation of enzyme supports on a cellulose basis with optimum properties: the reactive group is to result in a bond which produces little or no diminution of the enzyme activity. At the same time, the polyfunctional group brought to reaction during the functionalization forms a spacer of its own, namely an atom grouping which maintains the desired spacing from the cellulose chains and which permits an unhampered enzymatic activity of the acylases bound to them. Then, by selecting the molar ratio of the reactants, that degree of substitution of the hydroxyl group on the cellulose structure units can be achieved which produces the most favorable content of cleavage-active protein in the immobilizates. The possibility of preparing the best carrier for the particular acylase of varying origin by the synthesis of the cellulose carrier is of decisive importance to economical utilization: if the carrier contains on the one hand only a few groups capable of protein formation, the specific activity of the immobilizates is low. On the other hand, in the case of protein contents of an activity greater than the optimum, the active centers of the biocatalyst will remain inactive for steric and other reasons.

The groups of the functionalized cellulose prepared in accordance with the aforementioned Ser. No. 838,432 which are rendered capable of binding, such as for example carboalkoxy groups, namely, carbomethoxy, carboethoxy, p-nitroaryl or γ-aminopropyl groups, for example, can be coupled with acylases by known reactions. A collection of such enzymic transformation methods is presented by H. H. Weetall in Analytical Chemistry, Vol. 46, No. 7, pp. 602 A sqq (1974) under the title, "Immobilized Enzymes." If, for example, the functionalized cellulose contains carbomethoxy groups, the fixation of the acylase can be accomplished by means of the corresponding azide, which is obtainable from the hydrazide by reaction with nitrous acid. Setting out from cellulose carriers containing nitroaryl groups, acylases can be converted to an insoluble form by reducing the aromatic nitro groups to amino groups and diazotizing the latter, after which the diazonium salts can be reacted with the protein. Aminoaryl cellulose can furthermore be transformed to isocyanate derivatives by means of phosgene, or to isothiocyanate derivatives by means of thiophosgene. Both cellulose derivatives can enter into covalent enzyme-active compounds with acylase. γ-aminopropyl groups on the cellulose support can be reacted with glutardialdehyde and other compounds or they can be acylated with thiophosgene, for example, to form the isothiocyanate, after which these derivatives are capable of reaction with acylase.

The chemical reaction of the acylases with the functionalized cellulose must accordingly take place under the conditions known to be suitable for the reaction, which do not harm the acylases.

The reaction can be performed in the suspended phase.

Both refined acylases and technical acylase concentrates of varying degrees of purity can be used for the coupling. The binding of the acylases onto the reactive groups of the cellulose derivatives is performed in aqueous solutions whose pH is controlled and preferably buffered, in the neutral and weakly alkaline range, generally at pH 6.5 to 9.0, preferably at pH 7.0 to 8.5.

The temperatures during the coupling are generally between 0° C. and the limit determined by the thermal stability of the enzyme in question. The reaction time can be from several hours to several days.

In the case of a monoaminoalkyl-alkoxysilyl group, the binding of the acylases can be performed by the formation of Schiff bases or after reaction with, for example, thiophosgene to isothiocyanite as a thiourea derivative.

When the coupling is completed, the enzyme-active solids are washed thoroughly with buffer solutions and/or substrate solutions for the removal of adhering or loosely bound proteins. The buffer solutions have pH values, as a rule, between 6.5 and 8.0. Until they are used, the immobilizates are best preserved under buffer solutions, preferably between 0° and 10° C.

When used for the resolution of N-acyl-D,L-amino acids, the activity of the acylase immobilizates prepared in accordance with the invention usually decreases by a small fraction—no more than a few percent—of the initial activity. After that the acylase preparations are virtually constant in their activity.

It is a special advantage of the fixed acylases, in addition to their simplified preparation and the advantageous separability from the substrates, that the loss of the enzyme activity through degradation is slight. After the cleavage reaction, therefore, the activity is very substantially sustained, so that a frequent repetition of the cleavage with the same carrier-bound acylase is possible.

EXAMPLES

The activity given in the Examples 1–3 is measured in units of $10^{-6}$ moles (micromoles) of substance cleaved per minute.

EXAMPLE 1

10 g of functionalized cellulose, prepared by the reaction of linters cellulose, which had been dissolved in a mixture of dimethylsulfoxide and paraformaldehyde, with p-chloromethylbenzoic acid methyl ester at 50° C., in accordance with Example 1 (see infra) of the aforementioned Ser. No. 838,432, but having a content of 4.0 wt.-% of carbomethoxy groups, was suspended, with stirring, in a solution of 14 g of hydrazine hydrate in 300 ml of methanol for two days at 30° C. After removal of the hydrazide by centrifugation and thorough washing with methanol and then with water, the moist product was converted in a conventional manner to the azide with a solution of 10 g of sodium nitrite and 100 cm³ of 2 N HCl with ice cooling, and after the reaction was complete the latter was washed free of acid and centrifuged. The moist substance was stored in the refrigerator at 4° C. in a solution of 1.0 g of soluble acylase prepared from *Aspergillus orycae* (spec. activity 10 U/mg; substrate: N-acetyl-D,L-methionine) in 20 ml of 0.1 molar phosphate buffer ($NaH_2PO_4$ and $Na_2HPO_4$)

of pH 7. After three days the bottom sediment was removed by centrifugation. (The buffered acylase solution obtained after the removal by centrifugation of the enzyme-active solids can be reacted again with fresh reactive support until the activity is used up). The immobilizate was washed with 0.1 molar phosphate buffer at pH 7 until no enzyme activity could any longer be measured in the eluate, and it was preserved under phosphate buffer solution at 4° C. until it was used for cleaving. The enzyme activity of the immobilizate (37° C.; N-acetyl-D,L-phenylalanine as substrate) was 80 units per gram of moist material.

EXAMPLE 2

10 g of p-nitrobenzoyl cellulose, prepared by the acylation of cellulose dissolved in a mixture of dimethylsulfoxide and paraformaldehyde with p-nitrobenzoyl chloride at 70° C. in accordance with Example 3 (see infra) of the aforementioned Ser. No. 838,432, having a nitrogen content of 1.5% by weight, was heated with excess aqueous 1 wt.-% sodium dithionite solution at its boiling temperature for one hour. The suction filtered, reduced product was thoroughly washed with distilled water and diazotized, without drying, with aqueous 10% sodium nitrite solution of 2 N HCl, with ice cooling, in the usual manner. The acid-free, moist diazonium compound was placed in a solution of 1.0 g of soluble acylase prepared from *Aspergillus orycae* (spec. activity 15 units per mg, substrate: N-acetyl-D,L-methionine) in 50 ml of 1.0 molar phosphate buffer of pH 7, and preserved for 3 days at 4° C. After all solubles had been washed out, the enzyme activity of the moist immobilizate amounted to 102 units per gram (37° C., N-acetyl-D,L-phenylalanine as substrate).

EXAMPLE 3

10 g of linters cellulose functionalized by γ-aminopropylsilyl groups, prepared by the reaction of cellulose dissolved in dimethylsulfoxide and paraformaldehyde with γ-aminopropyltriethoxysilane at 80° C. pursuant to Ser. No. 838,432, and having a nitrogen content of 1.4 wt.-%, was acylated with a refluxing solution of 2 g of p-nitrobenzoyl chloride in 100 ml of chloroform with the addition of 1.5 g of triethylamine. The reaction product was reduced with sodium dithionite in the manner described in Example 2, after being thoroughly washed with chloroform, methanol and water, and it was then diazotized. The moist, acid-free product was reacted with the same amount of acylase solution of the same concentration by the method described in Example 2. The enzyme activity of the moist preparation amounted to 76 units per gram (37° C., N-acetyl-D,L-phenylalanine as substrate).

Examples 1 and 3 of Ser. No. 838,432 are as follows:

EXAMPLE 1

10 grams of powdered linters cellulose ("MN 200", manufactured by Macherey, Nagel & Co., Duren) were dissolved in a 500 milliliter flask equipped with stirrer, thermometer and electrical heater, in a mixture of 190 g of dimethylsulfoxide and 10 g of paraformaldehyde, at 50° C. At this temperature, after the addition of 0.1 g of finely powdered sodium hydroxide, a solution of 10 g of p-chloromethyl-benzoic acid methyl ester in 30 g of dimethylsulfoxide was added in portions over a period of 30 minutes. Then the mixture was stirred for four hours at 50° C. The reaction mixture, cooled to room temperature, was then poured into ethanol while the latter was being stirred vigorously. The solid was suction filtered, suspended repeatedly in ethanol until all the soluble substance had been removed, and dried. The yield was 10.6 g. The product was free of chlorine and acid.

According to analysis, there was a content of 8.2 wt.-% of carbomethoxy groups in the functionalized cellulose. Accordingly, 28.4% of the free hydroxyl groups of the cellulose had been etherified by the entry of the group:

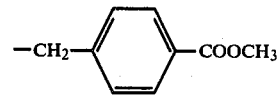

EXAMPLE 3

10 g of powdered linters cellulose ("MN 200") was dissolved in dimethylsulfoxide and paraformaldehyde as described in Example 1. After the addition of 5 g of p-nitrobenzoyl chloride and 0.05 g of sodium hydroxide, the mixture was stirred for two hours at 70° C., then heated at the boiling temperature for 30 minutes on the reflux condenser while a slow stream of nitrogen was passed through the apparatus. After standing overnight, the mixture was poured into a mixture of equal parts of ethanol and toluene by volume, with vigorous agitation. The precipitate was washed first with ethanol and then with water, and dried. The yield was 10.5 grams.

The nitrogen content in the product was 1.5 wt.-%, on the basis of the introduced nitrobenzoyl moiety.

What is claimed is:

1. Process of preparing carrier-bound acylase which comprises reacting a soluble acylase with a chemically bound reactive group of a cellulose derivative prepared by reaction of a hydroxyl group of cellulose with a reagent containing at least two reactive functional groups to provide said reactive group, the reaction of a hydroxyl group of cellulose and said reagent being performed by contacting the reagent with cellulose dissolved in dimethylsulfoxide containing polyhydroxymethylene for reaction of the cellulose and reagent to form said derivative.

2. Process of claim 1, wherein said soluble acylase is contained in an acylase substrate.

* * * * *